(12) United States Patent
Lee (10) Patent No.: US 9,168,493 B1
(45) Date of Patent: Oct. 27, 2015

(54) WASTE WATER TREATMENT SYSTEM

(76) Inventor: Brent Lee, Saratoga, CA (US)

( * ) Notice: Subject to any disclaimer, the term of this patent is extended or adjusted under 35 U.S.C. 154(b) by 841 days.

(21) Appl. No.: 13/338,141

(22) Filed: Dec. 27, 2011

Related U.S. Application Data (60) Provisional application No. 61/460,171, filed on Dec. 28, 2010, provisional application No. 61/446,711, filed on Feb. 25, 2011.

(51) Int. Cl.
*C02F 1/00* (2006.01)
*C02F 1/44* (2006.01)
*C02F 11/02* (2006.01)
(Continued)

(52) U.S. Cl.
CPC ............... *B01D 61/16* (2013.01); *B01D 33/37* (2013.01); *B01D 33/39* (2013.01); *B01D 36/00* (2013.01); *B01D 37/00* (2013.01); *B01D 65/00* (2013.01); *C02F 1/44* (2013.01); *C02F 11/02* (2013.01); *C02F 11/04* (2013.01); *C12M 1/128* (2013.01); *B01D 2311/02* (2013.01); *B01D 2311/04* (2013.01)

(58) Field of Classification Search
CPC ............ B01D 33/003; B01D 33/0016; B01D 33/0087; B01D 36/00; B01D 36/02; B01D 63/06; B01D 63/16; B01D 63/18; B01D 61/18; B01D 46/0041; B01D 50/002; B01D 2311/2688; B01D 2313/08; B01D 2315/02; B01D 2323/283; C12M 1/02; C12M 1/10; C12M 1/128; C12M 23/44; C12M 27/10; C12M 43/0027; C12M 45/02; C12M 45/04; C12M 45/09
USPC .................. 210/145, 173, 295, 259, 337, 338, 210/321.65, 321.68, 321.72, 619, 631, 632, 210/650, 773; 435/161, 162, 286.7, 289.3, 435/290.3, 308.1
See application file for complete search history.

(56) References Cited

U.S. PATENT DOCUMENTS 1,893,581 A * 1/1933 Court ............................. 210/145
3,396,103 A * 8/1968 Huntington ................... 210/652
(Continued)

FOREIGN PATENT DOCUMENTS

EP          2135938     * 12/2009     ............. C12M 1/107

OTHER PUBLICATIONS

Peter M. Wild and Geoffrey W. Vickers; "The Technical and Economic Benefits of Centrifugal Reverse Osmosis Desalination"; Desalination; 1992; pp. 33-40; vol. 89; Elsevier Science Publishers B.V., Netherlands.

(Continued)

*Primary Examiner* — Joseph Drodge
(74) *Attorney, Agent, or Firm* — Andrew D. Fortney; Central California IP Group, P.C.

(57) ABSTRACT

Methods and systems for treating waste water in residential, industrial and agricultural environments are disclosed. The methods and systems for treating waste water can be localized and self-contained with no need to channel sewage to a remote location. The waste water treatment methods and systems result in recycled clean water, concentrated effluent, and disposable solids. The recycled water can be used for landscaping and domestic use. The concentrated effluent can be channeled to an anaerobic digester to generate biogas, such as hydrogen, methane, and/or carbon dioxide, which can be used to generate power or as fuel for heating and/or cooking. The disposable solids may be used as fertilizer for farming or gardening.

21 Claims, 8 Drawing Sheets

(51) Int. Cl.

| | | |
|---|---|---|
| C02F 11/04 | (2006.01) | |
| C12M 1/10 | (2006.01) | |
| B01D 33/37 | (2006.01) | |
| B01D 33/39 | (2006.01) | |
| B01D 33/42 | (2006.01) | |
| B01D 36/00 | (2006.01) | |
| B01D 37/00 | (2006.01) | |
| B01D 61/16 | (2006.01) | |
| B01D 61/20 | (2006.01) | |
| B01D 65/00 | (2006.01) | |
| C12M 1/12 | (2006.01) | |

(56) References Cited

U.S. PATENT DOCUMENTS

| | | | |
|---|---|---|---|
| 3,955,755 A | 5/1976 | Breillatt, Jr. et al. | |
| 4,077,887 A | 3/1978 | Langvik | |
| 4,133,657 A | 1/1979 | Krogsrud | |
| 4,156,600 A | 5/1979 | Jacobson | |
| 4,160,732 A | 7/1979 | Maffet | |
| 4,287,058 A | 9/1981 | Larsen | |
| 4,592,848 A | 6/1986 | Pabst | |
| 4,708,801 A * | 11/1987 | Galaj | 210/636 |
| 5,516,426 A * | 5/1996 | Hull et al. | 210/256 |
| 5,543,087 A * | 8/1996 | Lee et al. | 261/87 |
| 5,562,758 A | 10/1996 | Awaji | |
| 5,670,043 A * | 9/1997 | Lee | 210/396 |
| 5,707,517 A | 1/1998 | Rolchigo et al. | |
| 7,282,146 B2 | 10/2007 | Mannheim et al. | |
| 7,306,735 B2 | 12/2007 | Baggott et al. | |
| 8,048,307 B2 | 11/2011 | Lee | |
| 8,308,953 B2 * | 11/2012 | Lee | 210/637 |
| 2002/0179516 A1 | 12/2002 | Behrendt et al. | |
| 2005/0056590 A1 | 3/2005 | Baggott et al. | |
| 2007/0039869 A1 | 2/2007 | Lovizzaro | |
| 2008/0047895 A1 | 2/2008 | Elefritz, Jr. et al. | |
| 2008/0245737 A1 | 10/2008 | Coulter | |
| 2008/0245738 A1 | 10/2008 | Coulter | |
| 2009/0107922 A1 | 4/2009 | Zhang et al. | |
| 2010/0044309 A1 * | 2/2010 | Lee | 210/636 |
| 2012/0058023 A1 * | 3/2012 | Hoglund et al. | 422/187 |

OTHER PUBLICATIONS

G. A. Karim and I. Wierzba; Abstract for "Methane-Carbon Dioxide Mixtures as a Fuel"; Aug. 1, 1992; Paper No. 921557; SAE International.

Ghazi A. Karim; "An Examination of the Combustion of Biogases and Low Heating Value Gas Fuel Mixtures", Nov. 8, 2010; 28 pgs.; International Conference on Energy and Automotive Technologies, Turkey.

* cited by examiner

WASTE WATER TREATMENT SYSTEM

RELATED APPLICATIONS

This application claims the benefit of U.S. Provisional Application Nos. 61/460,171, filed Dec. 28, 2010 and 61/446,711, filed Feb. 25, 2011, each of which is incorporated herein by reference in its entirety.

FIELD OF THE INVENTION

The present invention generally relates to the field of waste water treatment systems. More specifically, embodiments of the present invention pertain to methods and devices for treating waste water in residential, industrial and agricultural environments.

DISCUSSION OF THE BACKGROUND

Shortages of energy and water are significant global problems. Solutions are being developed to the problems, generally utilizing energy efficient technology to achieve balance with our earth. The present invention approaches its solution from often over-looked areas: household waste and farming waste.

The current state of the art technology is piping sewage (or waste water) to a centralized municipal waste water treatment plant, usually miles away. Capital costs of the plant, costs of channeling or transporting the waste water to the plant, and environmental concerns are a few of the issues which might put this type of system in a disadvantageous position in the foreseeable future.

SUMMARY OF THE INVENTION

Embodiments of the present invention relate to methods and apparatuses for processing waste water. More specifically, embodiments of the present invention relate to waste water treatment systems and methods of waste water treatment, power generation, and biogas (e.g., hydrogen, methane, carbon dioxide, etc.) production.

A first aspect of the present invention concerns an apparatus, comprising (a) a chamber for receiving waste water; (b) a plurality of filters, arranged radially around a central axis, configured to receive the waste water from the chamber and, upon being rotated around the central axis, retain elements of the waste water having at least a first minimum size and to allow a filtered mixture to pass through, the filtered mixture having particles therein with a size less than the first minimum size; and (c) a plurality of filtration modules, arranged radially around the central axis, configured to receive the filtered mixture and, upon being rotated around the central axis, separate a concentrate from the filtered mixture and produce substantially clean water from the filtered mixture, the concentrate having particles therein with a size greater than a second minimum size, the second minimum size being significantly smaller than the first minimum size.

A second aspect of the present invention concerns a method of processing waste water, comprising (a) introducing waste water into one or more chambers operably connected to a plurality of filters arranged radially around a central axis; (b) rotating the plurality of filters at a sufficient rotational speed to pass a filtered mixture through at least one of the filters, the filtered mixture having particles therein with a size less than a first minimum size, each filter being configured to retain elements of the waste water having a size greater than the first minimum size; (c) transferring the filtered mixture to a plurality of filtration modules arranged radially around the central axis; and (d) rotating the plurality of filtration modules and the filtered mixture at a sufficient rotational speed to separate a concentrate from the filtered mixture and produce substantially clean water from the filtered mixture, the concentrate having particles therein with a size greater than a second minimum size, the second minimum size being significantly smaller than the first minimum size.

The apparatuses and methods described herein provide a localized, self-contained solution to problems associated with waste water treatment and management. For example, the waste water treatment systems of the present invention can be built or situated with a building, structure, and/or a small community, and thus can process waste water locally without transporting the waste water to a remote site. This reduces the costs of waste water management as large-scale water treatment plants are not needed. Furthermore, the costs associated with maintaining and managing a water treatment system can be significantly reduced. In addition, the systems and apparatuses of the present invention enable the production of useful end-products of the water treatment process, such as reusable clean water, sources of renewable energy, and bio-fertilizer. The present methods and systems further enable a reduction in pollution and greenhouse gases, as well as waste odors and pathogens.

These and other advantages of the present invention will become readily apparent from the detailed description below.

DETAILED DESCRIPTION

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, and components, have not been described in detail so as not to unnecessarily obscure aspects of the present invention.

An innovative concept/design of a localized green resource station (the "station") is proposed herein, which may serve, for example, a typical residential high-rise building, an industrial or research facility, a farm, or a small community. As an example, the station may be situated in the basement of the high-rise building and may take the sewage or waste water from housing units above and process it, resulting in recycled clean water, concentrated effluent, and disposable solids. The water demand and economics will determine the grade of recycled water "cleanliness." For example, the recycled water can be used for landscaping and/or domestic use, or if acceptable, for drinking and cooking.

The concentrated effluent can be channeled to an anaerobic digester to generate biogas (e.g., methane and carbon dioxide), which in turn can be used as fuel for hot water heating, cooking, or any other suitable use. However, in this process, there may be solid waste contained in a filter (e.g., bag or other container) as a by-product. Some options for this waste include in situ use as fertilizer for farming or gardening, or collecting and transporting the waste to a relatively remote site for use (e.g., as fertilizer) or further processing by a disposal company.

This station can be built or installed in the basement of a building or other suitable location. In one example, the station can be about the size of a typical bedroom. In other implementations, the station may be built on an entire floor of a building, or housed in a separate building. In some implementations, the station may comprise a relatively small scale apparatus, and may have dimensions on a scale that is 1/10 to 1/2 the exemplary dimension ranges discussed in detail herein. In other embodiments, the station may comprise a relatively large-scale apparatus, for example, having dimensions on a scale that is 2 to 10 times the exemplary dimension ranges described herein. In some instances, the station may include an array of water purification apparatuses (e.g., 2, 3, 4, or more) that may receive a common inflow or separate inflows, and collect purified water in a common storage tank or separate tanks. In such embodiments, the array of room-sized apparatuses can meet the water treatment needs of a larger building or complex, a farm, or any other building or community, and may reduce the down-time and/or cost(s) of the system. The station may be self-contained, with no need to channel the sewage to a remote location. In general, the maintenance of the station is relatively simple. For example, remote monitoring can be set up, along with periodic collection of the solid waste bags, periodic checking and/or replacement of the fine filter cartridges, etc.

Overall, the operation of the present waste water treatment system or station can be relatively simple, and the benefits may include: (1) producing reusable clean water and renewable energy, (2) reducing pollution and greenhouse gases, (3) reducing waste odors and pathogens, and (4) transforming waste into valuable bio-fertilizer. The apparatuses and methods of the present invention may reduce the retention time of the sewage or waste water, and may increase the production rate or yield of the useful end-products of the process.

As a result, the water filtered in accordance with the present invention may contribute to about half of the household or farm usage, and biogas generated from the waste may contribute significantly to the household/farm demand. For example, "Methane-Carbon Dioxide Mixtures as a Fuel" (Karim & Wierzba, 1992) and "An Examination of the Combustion of Biogases and Low Heating Value Gas Fuel Mixtures" (Karim, 2010) discuss the use of methane-carbon dioxide mixtures as fuel. Alternatively, the carbon dioxide can be removed (e.g., by bubbling the gas mixture through water or dilute alkali such as dilute aqueous ammonia/ammonium hydroxide, or by scrubbing the gas mixture by passing it over a carbon dioxide remover such as calcium hydroxide; more sophisticated [e.g., catalytic and/or recyclable] $CO_2$ scrubbers may also be used). Moreover, the cost of building a waste water treatment plant can be saved or spread out over a larger community or area. Nevertheless, it may be premature to calculate the benefits on a global scale, which are expected to be enormous.

For the sake of convenience and simplicity, the terms "apparatus" and "system" are generally used interchangeably herein, and use of one generally includes the other, unless the context necessarily indicates otherwise, but these terms generally are given their art-recognized meanings. Also for the sake of convenience and simplicity, the terms "effluent," "waste water," and "sewage" are also generally used interchangeably herein, but are generally given their art-recognized meanings.

The invention, in its various aspects, will be explained in greater detail below with regard to exemplary embodiments.

An Exemplary Apparatus

A first aspect of the present invention relates to an apparatus for processing waste water (e.g., a waste water treatment system). The apparatus generally includes a chamber for receiving waste water and a plurality of filters arranged radially and in a fixed position around a central axis or shaft. The filters are configured to receive the waste water from the chamber, and when rotated around the central axis, the filters retain elements of the waste water having a least a first minimum size. The filters are also configured to allow a filtered mixture (e.g., having particles therein with a size less than the first minimum size) to pass through.

The apparatus further includes a plurality of filtration modules which are arranged radially around the central axis. The plurality of filtration modules are configured to receive the filtered mixture and, upon being rotated around the central axis, separate a concentrate from the filtered mixture and produce substantially clean water from the filtered mixture. In general, the concentrate has particles therein with a size greater than a second minimum size, where the second minimum size is significantly smaller than the first minimum size. In some implementations, the apparatus may include a device (e.g., a motor, hand crank, foot pedal, etc.) configured to provide rotational force for the central axis or shaft. In some variations, the apparatus may also include a clutch that varies the rotational speed ratio between the upper portion and the lower portion of the apparatus.

Figure 1A:
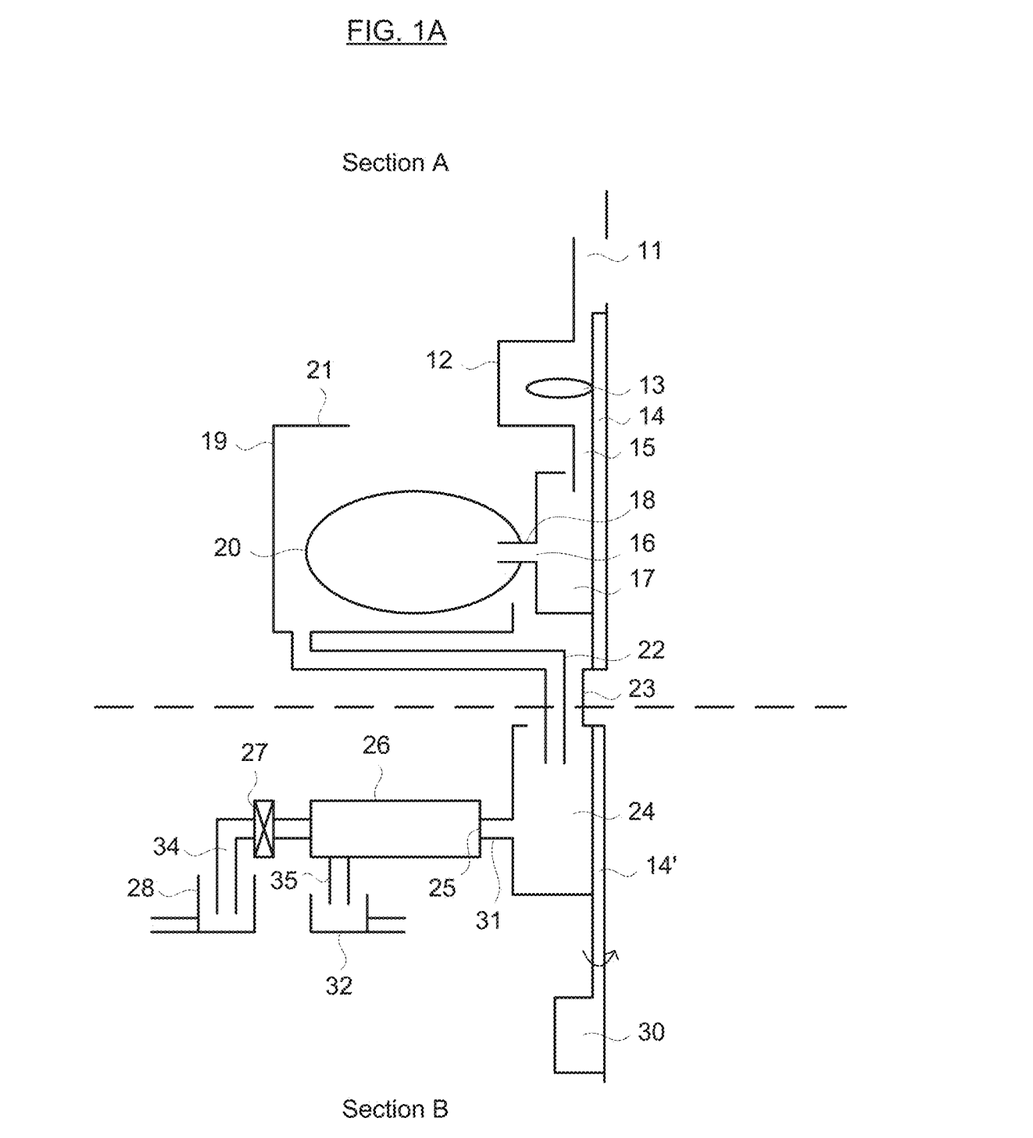
FIG. 1A is a diagram showing a radial cross-sectional view of the interior of an exemplary waste water treatment system according to the present invention.
Figure 1B:
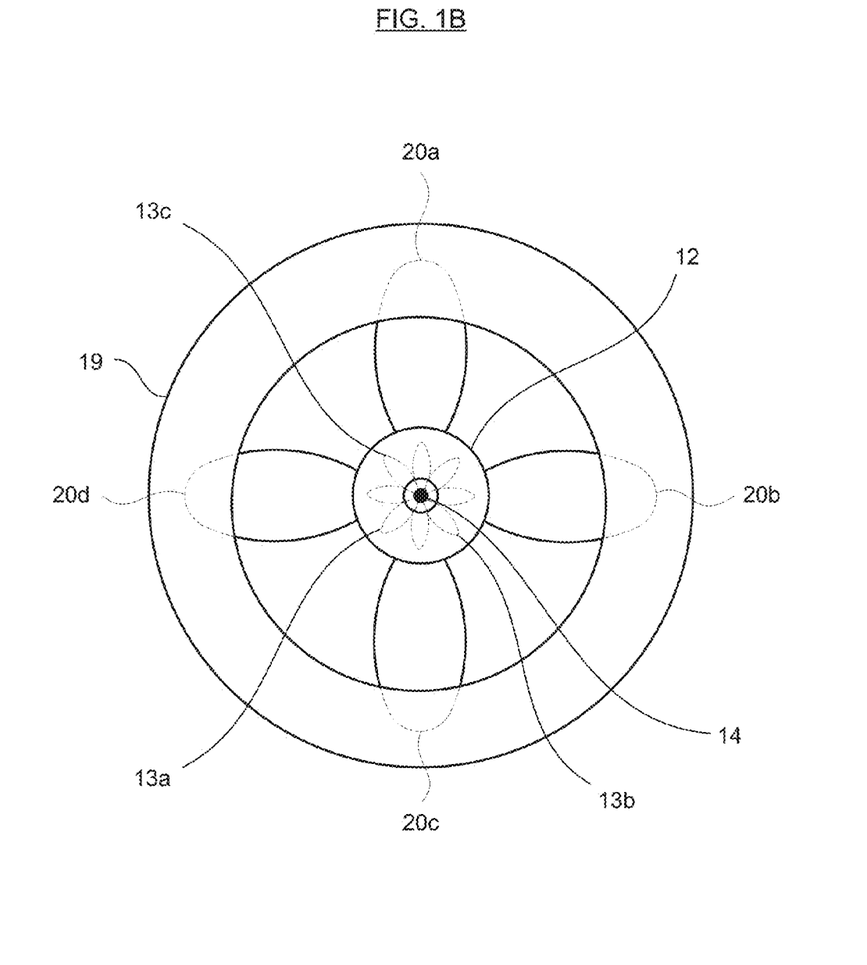
FIG. 1B is a top-down view of the upper portion (Section A) of the exemplary waste water treatment system shown in FIG. 1A.
Figure 1C:
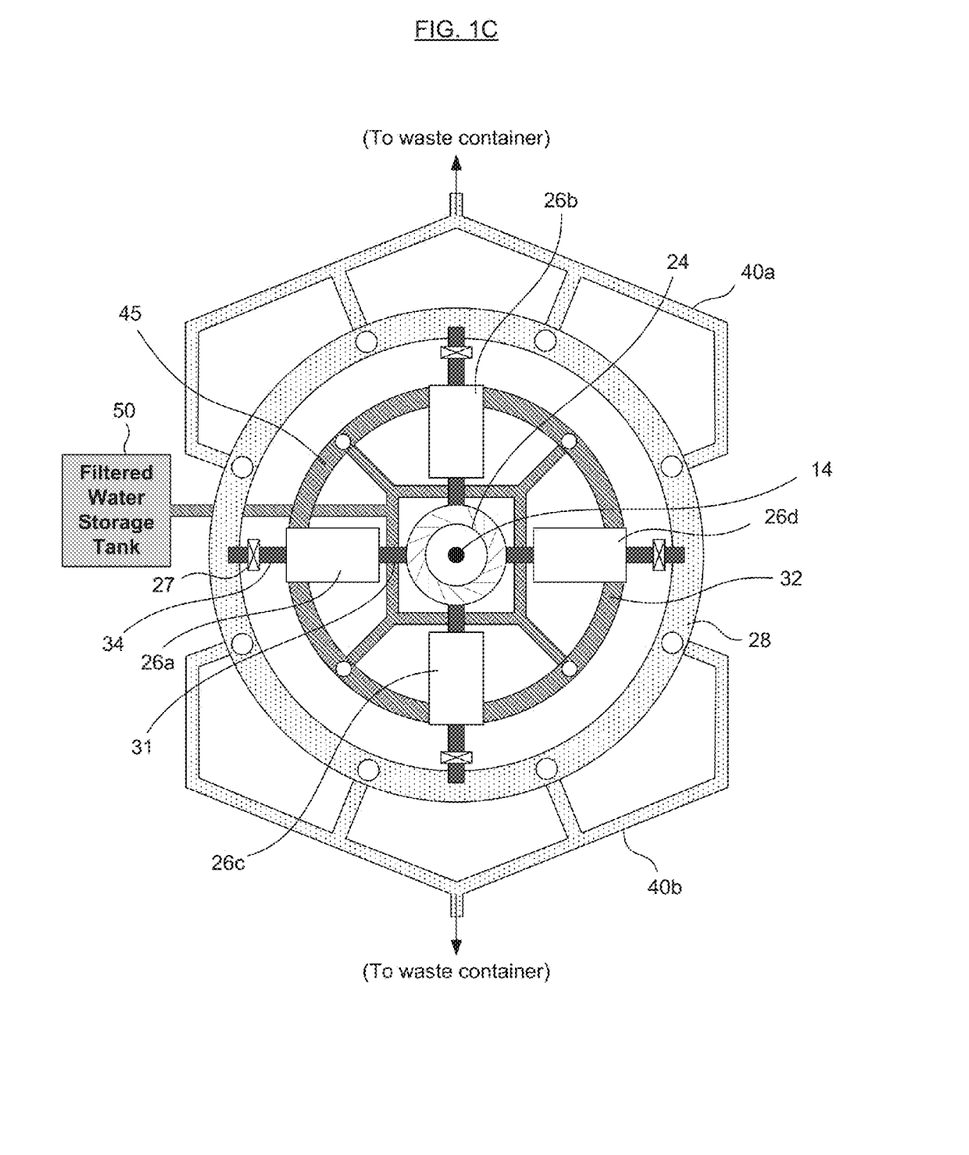
FIG. 1C is a top-down view of the lower portion (Section B) of the exemplary waste water treatment system shown in FIG. 1A.

The apparatus is described in detail herein with reference to FIGS. 1A-1C. Specifically, FIG. 1A shows a cross-sectional side view of the apparatus along its radius, and FIGS. 1B and 1C show top down views of the upper section (Section A) and the lower section (Section B) of the apparatus shown in FIG. 1A. Referring first to FIG. 1A, in exemplary embodiments, the apparatus comprises a chamber 12 for receiving and mixing or blending waste water from an inlet 11. The inlet 11 may comprise a tube, pipe or other suitable structure configured to allow influent to flow into the mixing chamber 12. The inlet 11 may comprise metal, plastic, rubber, ceramic (clay), or any other suitable material known in the art, and have a diameter of from 4 to about 12 inches (100-300 mm). Although not shown in FIG. 1A, the apparatus may also include a screen or mesh over or within the inlet 11, which is configured to remove large objects (e.g., greater than 1 inch [2.5 cm] in length, width, and/or height) from the waste water as it passes through the screen into the mixing chamber 12. Such a screen or mesh may be made from wire and be manufactured or configured to form openings therein of from 1/2 to 1 inch (1.25 to 2.5 cm) across.

Referring now to FIG. 1B, the (mixing) chamber 12 is generally circular and continuous around a central axis 14 (e.g., cylindrical or toroidal), which spans the length or height of the apparatus (as shown in Sections A and B of FIG. 1A). However, the mixing chamber 12 may have any other suitable shape (e.g., square, rectangular, etc.) and/or size appropriate for the apparatus. For example, in some exemplary embodiments, the mixing chamber 12 may have an outer diameter of from about 2 to 0.5 feet (60 cm to 1.5 m), or any value or range of values therein. The wall of mixing chamber 12 may have a thickness of from about 0.1 to about 2.5 cm, or any value or range of values therein. The height of the mixing chamber 12 may be about 0.5 to about 5 feet (15 cm to 1.5 m), or any value or range of values therein. The wall of mixing chamber 12 may be made from metal, plastic, ceramic (clay), or any other suitable material known in the art, and in some exemplary embodiments, the mixing chamber 12 may have a protective and/or non-stick coating on the interior and/or exterior surfaces of the chamber. In some implementations, the mixing chamber can be fixed in space, for example where the axis 14 and blades 13 rotate while the mixing chamber 12 remains still. In other implementations, the mixing chamber 12 can rotate with the axis 14.

Referring to FIG. 1A, in some implementations, the mixing chamber 12 includes a rotating mechanism or device 13 that is configured to mix or blend the waste water entering the mixing chamber 12 through inlet 11. For example, the rotating mechanism or device 13 may comprise a plurality of rotating blades, paddles, beaters, or any other rotating structure capable of mixing, blending, or stirring the influent in the mixing chamber 12. In general, the mechanism (e.g., blades) functions to thoroughly mix the contents of the waste water and ensure more efficient filtration by the filters 20.

Referring now to FIG. 1B, in some embodiments, the rotating device can include multiple blades or paddles (e.g., 13a-13c) arranged radially and/or circumferentially around the central axis 14, at equal distances and/or angles from each other. Although FIG. 1B shows an apparatus with 8 blades, the apparatus is not limited as such. On the contrary, the mixing chamber 12 may have any number of blades desired. The blades 13 can have any length (e.g., 6 inches to about 2 feet [15 to 60 cm], or any value or range of values therein) suitable for mixing the influent in the mixing chamber 12. Although not shown in the drawings, in some embodiments, the blades 13 have varying lengths. For example, one subset of the blades may have a first length, and another subset a second length, where the first length is longer or shorter than the second length. The blades 13 can have any suitable shape capable of mixing or blending the waste water (e.g., flat, curved, simple cylindrical rods, cork-screw shaped, beater shaped, etc.). Although not shown in the figures, in some variations, multiple blades, paddles, or other rotating structures can be arranged in a vertical direction. As the axis spins, the attached blades 13 also spin and mix the waste water. The device or motor 30 and/or the clutch 23 control the speed of rotation as discussed in detail below. The blades or paddles may be made using metal, plastic, wood, ceramic (e.g., a hardened ceramic), rubber, or any combination thereof.

Referring again to FIG. 1A, the central axis 14 may comprise a metal, a plastic, ceramic or other suitable rigid material that is capable of supporting the various components of the apparatus attached thereto. In addition, the central axis 14 may have any suitable shape, length, and/or diameter, as will fit and support the apparatus. For example, the central axis 14 may be of from about 3 to 10 feet (90 cm to 3 m) in length (or any value or range of values therein), and may be about 1 to 6 inches (2.5 to 15 cm) in diameter (or any value or range of values therein). The central axis 14 is configured to rotate or spin the chambers and/or filters of the apparatus at a rate suitable to mix, separate, and/or filter the waste water into various components, as described in detail herein.

As shown in FIG. 1A, in some implementations, the central axis 14 may include or otherwise be attached to a device 30 (e.g., a motor, hand crank, foot pedal, etc.) configured to provide rotational force for the central axis or shaft 14. For example, the central axis 14 may rotate at a rate of from about 50 rpm to about 50,000 rpm (e.g., 100 to 25,000 rpm, 1,000 to 10,000 rpm, 5,000 to 7,500 rpm, or any value or range of values therein). In some variations, the apparatus may also include a clutch 23 that separates the central axis or shaft into the upper segment (reference character 14 shown in Section A of FIG. 1A) and the lower segment (reference character 14' shown in Section B of FIG. 1A). The clutch 23 is generally configured to vary the rotational speed ratio between Section A and Section B. For example, the speed ratio between Section A and Section B may be from 1:1 to 1:1,000, or any range therein, and the speed ratio may be in either direction (Section A to Section B or Section B to Section A). In some embodiments, the clutch 23 may comprise a mechanism or device (e.g., mechanical, physical, or electronic) that is configured to engage and/or disengage the differential turning mechanism of the clutch as desired.

Referring again to FIG. 1A, in some exemplary embodiments, the mixing chamber 12 is connected to a second chamber 17 by an exit channel 15. In such embodiments, the second chamber 17 is generally situated beneath the mixing chamber 12 so that the mixed waste water can exit the mixing chamber 12 and flow by gravity into the second chamber 17. Like the mixing chamber 12, the second chamber 17 is continuous around the central axis 14, and may have any suitable shape (e.g., circular, cylindrical, square, rectangular, etc.) and size that fits within the apparatus. For example, the second chamber 17 may have a radius (i.e., from the axis to the outer edge of the chamber) of from about 1 to 2 feet (30 to 60 cm) and a height of from about 1 to 3 feet (30 to 90 cm), or any value or range of values therein. The second chamber 17 is attached to the central axis 14, and generally rotates at the same rate as the central axis 14. The second chamber 17 may be made using any material described above with regard to the mixing chamber 12, and may include a protective and/or non-stick coating on its interior and/or exterior surfaces.

The second chamber 17 is connected to a third chamber 19 by an outlet 16 and a tube or pipe (e.g., connector 18), which is generally arranged on the outside of the second chamber 17, as shown in FIG. 1A. The outlet 16 may comprise a tube, pipe, opening or any other connecting mechanism known in the art, and may be made using any suitable material (metal, plastic, ceramic, rubber, etc.) known in the art. In exemplary embodiments, the outlet 16 and/or the connector 18 may have a diameter of from about 1 to about 6 inches (2 to 15 cm), or any value therein. The outlet 16 may have the same diameter as the connector 18, or in some instances the outlet 16 and the connector 18 may have different diameters. In some embodiments, the outlet 16 is positioned in a lower region of the housing of chamber 17. Such positioning may ensure a more complete removal of solid material to be filtered or separated (e.g., in chamber 19 as described below). For example, material that may be more dense or larger in size (e.g., that was not removed by the screen in inlet 11) may be trapped in the chamber 17, and might not flow freely through the outlet 16. Positioning the outlet 16 near the bottom of the second chamber 17 may facilitate removal of such waste materials. In the alternative, any solid materials trapped in the bottom portion of the second chamber 17 may be removed by another mechanism, for example, by opening a trap (e.g., a bottom flap or door, not shown in the figures) in the housing of second chamber 17 and running clean water through the apparatus.

As shown in FIG. 1B, in exemplary embodiments, the third chamber 19 is generally circular and continuous around the central axis 14 (e.g., cylindrical or toroidal). However, the third chamber 19 is not limited as such, and may have any suitable size and/or shape (e.g., as described herein, such as square, hexagonal, octagonal, etc.). For example, the third chamber 19 may have a diameter of about 3 to 12 feet (1 to 3.5 m), or any value or range of values therein. In some variations, the third chamber 19 has a height of from about 1 to 6 feet (30 cm to 2 m), or any value or range of values therein. In some implementations, the third chamber 19 can be fixed in space, for example where the axis 14 and filter(s) 20 rotate while the third chamber 19 remains still. In other implementations, the third chamber 19 can rotate with the axis 14. The third chamber 19 may have a lip or an overhang 21 having a width of about 0.5 to 6 feet (15 cm to 2 m). The lip or overhang 21 may result in an opening in the third chamber 19 exposing the inside of the chamber 19 and the filters 20. Such an opening may reduce gas build-up inside the chamber, and may allow facile observation and maintenance of chamber 19 and the filters 20. In some embodiments, the third chamber 19 may have a continuous upper surface so that the upper surface of the chamber 19 is closed, or alternatively, the upper surface can be completely open. The third chamber 19 can be made using any suitable material known in the art and/or as described herein with regard to the system chambers. In some exemplary embodiments, the third chamber 19 includes a protective and/or non-stick coating on one or more of its inner surfaces.

In exemplary embodiments, the apparatus also comprises one or more filters or filtering devices 20, as shown in FIGS. 1A and 1B. In general, the one or more filters 20 are configured to receive the waste water having large and small particulates/contaminants therein from the second chamber 17. For example, as shown in FIG. 1A, the filtering device(s) 20 may be connected to the second chamber 17 by a connector 18, which in exemplary embodiments, is at about a 90° angle to the exit channel 15, and the vertical wall of second chamber 17, as shown in FIG. 1A. The connector 18 may comprise a tube, pipe, opening or any other connecting mechanism known in the art, and may comprise any suitable material (metal, plastic, ceramic, rubber, combinations thereof, etc.) known in the art. The filtering devices 20 may be fastened, attached, or otherwise connected to the connector 18 by any suitable mechanism known in the art. For example, in one embodiment, the filtering devices 20 may be fitted with one or more quick-connect fittings. In another example, the filter can be held at connector 18 by a band, ring clamp, or other attachment device. In such embodiments, the connector 18 may be configured with an external lip to mechanically retain the band (or clamp or other device) on the connector 18. Upon rotation around the central axis 14 (e.g., as previously described herein), the filters 20 are configured to retain elements of the waste water having at least a first minimum size (e.g., at least about 10 µm, 20 µm, 50 µm, or any value between 10 and 50 µm) and to allow a filtered mixture to pass through.

As shown in FIG. 1A, the filtering device 20 may be housed within the third chamber 19, and attached to or otherwise associated with the second chamber 17. In exemplary embodiments, the filtering device(s) 20 may comprise a coarse filter, a bag, or any other suitable filtering device known in the art. For example, in one variation, the filter 20 comprises a bag (preferably disposable, e.g., cloth) that may hold the solids (e.g., material greater than 50 µm in length and/or width) in the waste water and allow fluid to pass through, which may be collected in the third chamber 19. The bags may comprise or consist essentially of a biodegradable material, to enable more environmentally friendly disposal of the solids collected in the coarse filter 20. The opening of the bag 20 (e.g., as fitted onto the connector 18), may be secured by a device such as an elastic band that automatically closes the opening of the bag 20 when disengaged from pipe or connector 18 to prevent spillage of the contents of the bag 20. The filter(s) or bag(s) 20 may have a length of from about 1.5 to 7 feet (45 to 2.5 m) and a width or diameter of from about 1 to 4 feet (30 to 1.5 m) or any value or range of values that will fit within the third chamber 19 and effectively filter the waste water. The filter(s) or bag(s) 20 can have any suitable shape described herein. For example, the filter(s) or bag(s) may be circular, oval, egg or balloon shaped, square, rectangular, quadrilateral, trapezoidal, triangular, hexagonal, octagonal, etc.

Referring now to FIG. 1B, in some implementations, the apparatus can include a plurality of filters (e.g., reference characters 20a-d) arranged radially and/or circumferentially around the central axis 14 of the apparatus, generally at equal distances and/or angles from each other. Although not shown in the figures, in other variations, the apparatus may comprise multiple filters arranged in a vertical direction. The apparatus shown in FIG. 1B includes four filters 20a-d. However, the invention is not limited as such. On the contrary, the apparatus may have any number of filters or filtering devices, as desired. As the axis 14 spins, the filters 20a-d also spin and filter or separate the solid waste from the waste water. Larger solids are retained in the filters 20a-d, and a filtered mixture passes through and is collected in the third chamber 19. The device/motor 30 and/or the clutch 23 control the speed of rotation of the filters 20a-d, as previously discussed.

Referring again to FIG. 1A, the third chamber 19 may be connected to a lower (fourth) chamber 24 by a connector path 22. In some exemplary embodiments, the lower chamber 24 is situated below the third chamber 19, as shown in FIG. 1A. The connector path 22 may comprise a tube, pipe, hose, or other suitable device configured to allow the filtered fluid stored in the third chamber 19 to be channeled to the lower chamber 24, and may have a diameter of from about 1 to about 6 inches (2.5 to 15 cm), or any value therein. Furthermore, the connector path 22 may be comprise any suitable material (plastic, metal, rubber, ceramic [clay], a combination thereof, etc.) known in the art, and may have a protective and/or non-stick coating on its interior and/or exterior surfaces. The connector path 22 may have a substantially horizontal portion below the third chamber 19, and may also have first and/or second substantially vertical portions configured to carry filtered water from the third chamber 19 to lower chamber 24. In some embodiments, the substantially horizontal portion may be slightly sloped (e.g., up to about 10° relative to horizontal). The second substantially vertical portion generally extends into lower chamber 24, as shown in FIG. 1A.

In exemplary embodiments, the lower chamber 24 is generally circular and continuous around the central axis 14 (e.g., cylindrical or toroidal), as shown in FIG. 1C. However, the lower chamber 24 may have any suitable shape or size described herein with regard to chambers of the apparatus. For example, the lower chamber 24 may have a radius (i.e., from the axis to the outer edge of the chamber) of from about 1 to 3 feet (30 cm to 1 m) and a height of from about 1 to 4 feet (30 cm to 1.5 m), or any value or range of values therein. In general, as shown in FIG. 1A, the lower chamber 24 has a continuous opening in the upper surface to accommodate the second substantial vertical portion of the connector path 22 (e.g., tube, pipe, etc.) as the lower chamber 24 rotates around the central axis 14.

In exemplary embodiments, the apparatus further comprises one or more fine filtration modules 26 arranged radially and/or circumferentially around the central axis, at equal distances and/or angles from each other. The fine filtration module(s) 26 may be thought of as the "heart" of the system. Specifically, the fine filtration modules 26 are configured to receive the filtered mixture from the lower chamber, and upon being rotated around the central axis, separate a concentrate from the filtered mixture, and produce substantially clean water from the filtered mixture. The filtration modules 26 separate substantially clean water from the filtered mixture, producing a concentrate that generally has particles therein with a size greater than the pores of the filtration modules 26 (e.g., a second minimum size of at most about 1 μm, about 0.1 μm, or any value less than 1 μm). The second minimum size is significantly smaller than the first minimum size described above.

To illustrate, referring again to FIG. 1A, least one filtration module 26 (e.g., a fine filtration module, filtering device, or cartridge) is connected to the lower chamber 24 at the side by a connector 25. In exemplary embodiments, the fluid can flow from the lower chamber 24 to the fine filtration module(s) 26 through a conduit (e.g., a pipe or tubing) 31. For example, the conduit 31 may comprise a metal, plastic, or ceramic pipe, rubber tubing, etc. In general, the pipe or tubing 31 has a diameter of from about 1 to about 6 inches (2.5 to 15 cm), or any value therein. In some embodiments, the pipe or tubing 31 is positioned in a lower region of the housing of lower chamber 24. As described above with regard to second chamber 17, such positioning may ensure a more complete removal of solid material, contaminants, or impurities, to be filtered (e.g., in chamber 26 as described below). For example, material that may be more dense or larger in size (e.g., that was not removed by the coarse filter(s) 20) may be trapped in the lower chamber 24, and might not flow freely through the pipe or tube 31. Positioning the pipe or tube 31 near the bottom of the lower chamber 24 may facilitate removal of such waste materials. In the alternative, any solid materials trapped in the bottom portion of the lower chamber 24 may be removed by another mechanism, for example, by cleaning the chamber using a trap with a bottom flap, door, or opening in the housing of lower chamber 24 (not shown in the figures).

Referring again to FIG. 1C, in some implementations, the apparatus can include a plurality of fine filtration modules (e.g., reference characters 26a-d) arranged radially and/or circumferentially around the central axis 14 of the apparatus, generally at equal distances and/or angles from each other. Although not shown in the figures, in other variations, the apparatus may comprise multiple fine filtration modules arranged in a vertical direction. The apparatus shown in FIG. 1C includes four fine filtration modules 26a-d. However, the invention is not limited as such. On the contrary, the apparatus may have any number of filters or filtration devices 26a-d as desired.

Each of the fine filtration modules 26a-d may have any suitable size and/or shape. For example, in one exemplary embodiment and as shown in FIG. 1C, the fine filtration modules 26a-d may have a cylindrical shape with a length of from about 1 to 3 feet (30 cm to 1.5 m), a width (and/or diameter) of from about 4 inches to 1.5 feet (10 to 50 cm), and/or a volume of from 0.03 to 1.7 cubic feet (0.7 to 100 liters), or any value or range of values therein. However, the shape of the fine filtration modules is not limited, and the fine filtration modules may have any cross-sectional shape known in the art (e.g., circular, oval, triangular, etc.). In some instances, two or more filtration modules can be linked end-to-end (e.g., to increase the efficiency of the purification process).

The fine filtration modules 26a-d can be made using any suitable material known in the art (e.g., metal, plastic, ceramic, etc.), and in some exemplary embodiments, the fine filtration modules include a protective, non-stick, and/or metal coating on the interior and/or exterior surfaces. The rotation of the apparatus generates centrifugal force and/or takes advantage of the Coriolis effect to push the waste water to be filtered through the filtration material or membrane in filter modules 26a-d and separate the liquid from the particulate matter. Thus, the rotation of the apparatus (including the fine filtration devices 26a-d) can work in conjunction with the Coriolis effect to increase the pressure differential and/or rate of flow of influent across the inner surface of the fine filtration devices and/or membrane (see also U.S. Pat. No. 8,048,307, co-owned by Applicant, the relevant portions of which are incorporated herein by reference).

Figure 4A:
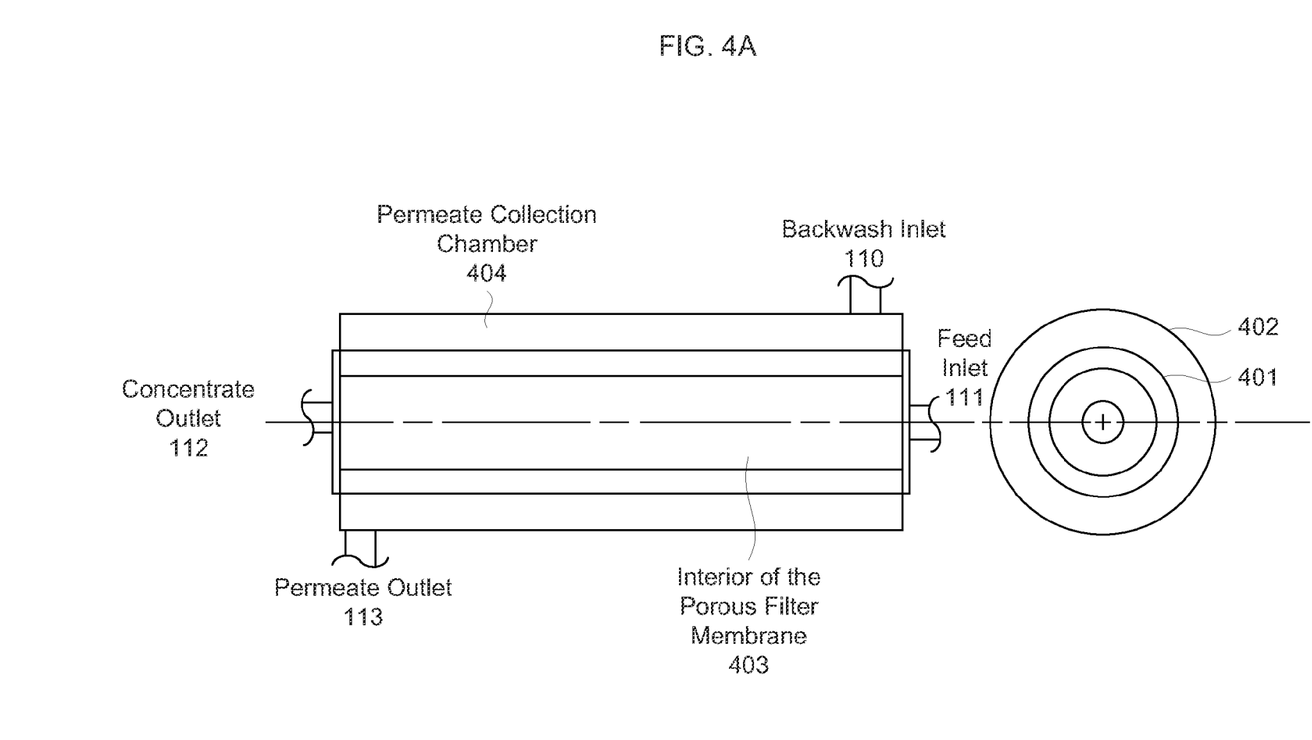
FIG. 4A shows a cross-sectional view of one exemplary embodiment of a cylindrical filter cartridge, including a single tubular filter membrane or a plurality of concentric tubular filter membranes.

FIG. 4A shows an exemplary embodiment of a filter cartridge. The filter cartridge generally has a tubular shape with a central axis, in which the cross-section transverse to the central axis may be any shape (e.g., square, rectangular, circular, oval, hexagonal, octagonal, irregular [e.g., to fit within certain dimensions or in a certain arrangement around body 106], etc.), but preferably the filter cartridge is cylindrical. The feed inlet 111 is directly connected to an inner chamber of the filter cartridge 109, which is generally the interior region of a porous filter 401. The inner chamber is isolated from the outer chamber (defined by the outer wall 402) of the filter cartridge by the porous filter 401 and seals or caps at one or both ends of the filter 401. The porous filter 401 also has a tubular shape with a central axis, in which the cross-section transverse to the central axis may be any of a wide variety of shapes (e.g., square, rectangular, circular, oval, hexagonal, octagonal, etc.), but preferably the porous filter 401 is also cylindrical. The seal(s) have openings for the inlet 111 at a near end of the filter 401 and a concentrate outlet 112 at a distal end of the filter 401 (when the concentrate outlet 112 has an outer diameter less than the inner diameter of the filter 401). The separation of the inner and outer chambers of the filter cartridge allows only a permeate (i.e., a filtered fluid) to pass through the porous filter 401 into the outer chamber, where a permeate outlet 113 (which is connected to the outer chamber) transports the permeate to a collection vessel or chamber. The distal end of the porous filter 401 is connected to a concentrate outlet 112, where a concentrate from within the porous filters 401 can be drained or collected during filtration (but after the influent has passed through the filter 401).

Figure 4B:
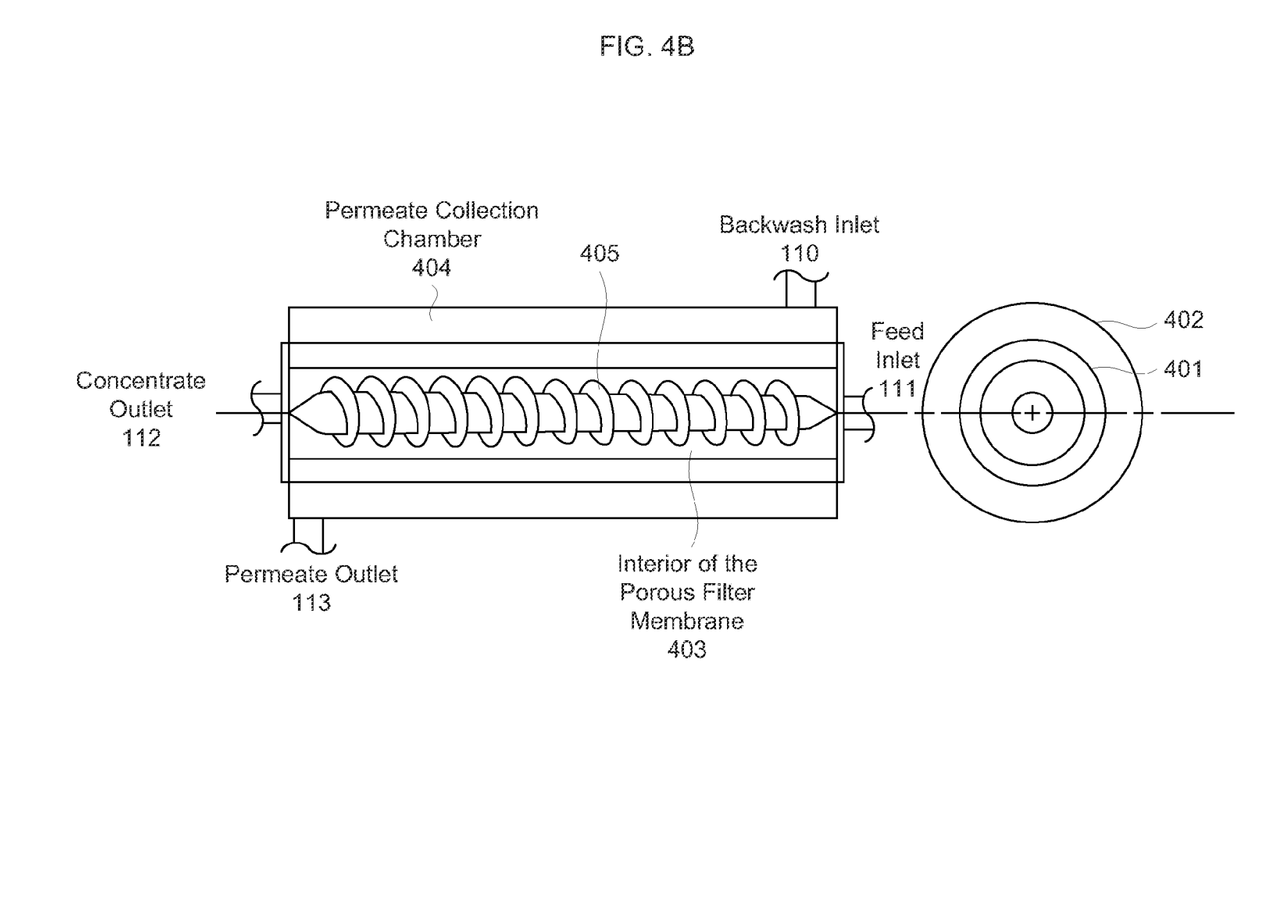
FIG. 4B shows a cross-sectional view of an exemplary alternative embodiment of a cylindrical filter cartridge, including a screw-shaped or spiral insert, placed in the filter membrane.

FIG. 4B shows an exemplary alternative embodiment of a cylindrical filter cartridge, including a screw-shaped, helical or spiral insert 405 in the filter membrane. In one embodiment, insert 405 has an orientation substantially the same as the spiral flow of influent through the interior 403 of the membrane 401. Typically, the insert is fixed and/or stationary within the interior 403 of the filter membrane 401. The insert 405 may have essentially any number of turns or threads compatible with the design of the filter of FIG. 4B. It is believed that the insert 405 works in conjunction with the Coriolis effect to increase the centrifugal force and/or rate of flow of influent across the inner surface of the membrane 401.

Figure 5:
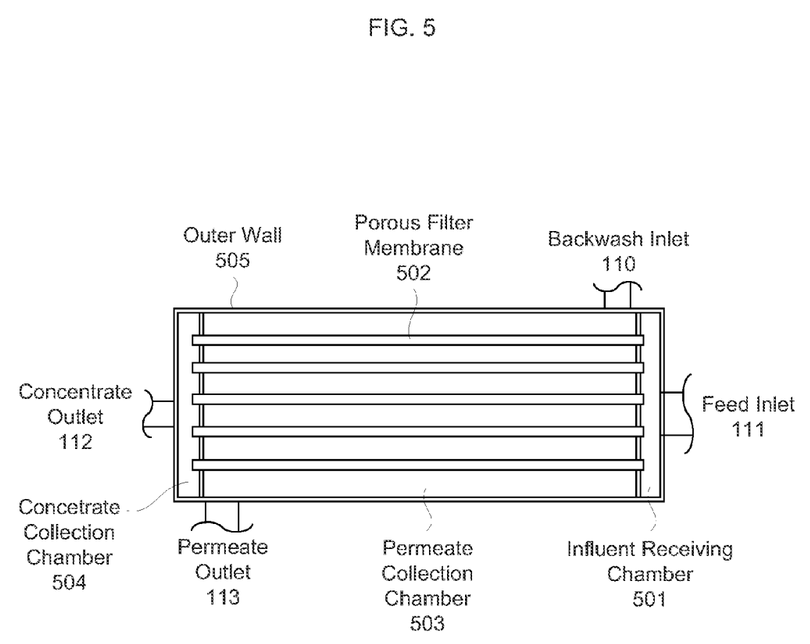
FIG. 5 shows a cross-sectional view of an alternative exemplary embodiment of a cylindrical filter cartridge, including multiple tubular filter membranes.

FIG. 5 shows an alternative embodiment of a filter cartridge. The feed inlet 111 is directly connected to an influent receiving chamber 501 of the filter cartridge. The receiving chamber 501 is connected to a plurality of porous filters 502 and is isolated from a permeate collection chamber 503. The filters 502 may be arranged concentrically in one or more cylinder-shaped arrangements, or the filters may be bunched together in a substantially parallel, but somewhat random, arrangement running down the length of the permeate collection chamber 503. This arrangement allows the influent to pass from the receiving chamber 501 into the porous filters 502, where the permeate passes through the porous filters 502 and into the permeate collection chamber 503. The distal ends of the porous filters 502 are connected to a concentrate collection chamber 504, where a concentrate from within the porous filters 502 can be collected during a filtration process. The porous filters 502 may have pinched, narrowed or drawn-down distal ends, in order to reduce the diameter of the outlet hole and increase the fluid pressure within the porous filters 502. (The same technique may be applied to the exemplary filter cartridge of FIG. 4A.) The concentrate collection chamber 504 receives the concentrate from each of the filters 502, and is attached to the concentrate outlet 112 for draining or transporting the concentrate to an external locations (e.g., to be pumped or otherwise fed back into the influent catch 102).

The outer wall (e.g., 402 or 505) of the filter cartridge comprises a rigid material that can withstand rotation of the centrifugal filtration apparatus at high speeds, and that is substantially non-reactive with the permeate. The outer wall may comprise a rigid polymeric, fiberglass, or metal (e.g., stainless steel) housing. The porous filters 401 or 502 may comprise a porous filter membrane having a pore size in a range of from about 0.0005 to about 0.1 µm, about 0.01 to about 100 µm, 0.1 to about 50 µm, about 1 to 500 µm, or any other range of values therein. The porous filter membranes may also have a pore distribution of in the range of from about 10 to about 10,000,000 pores/cm$^2$, about 100 to about 100,000 pores/cm$^2$, or any other range of values therein.

There are many commercially available filtration modules in the market. Some examples include GE Ultrafiltration ZEEWEED® 500 Membrane, GE Ultrafiltration ZEEWEED® 1000 Membrane, GE Ultrafiltration ZEEWEED® 1500 Membrane; FIBERFLO® Hollow Fiber Cartridge Filters, and AMI® Membranes (reverse osmosis filters), from Applied Membranes, Inc.

In exemplary embodiments, the apparatus or system may further include a plurality of collectors (e.g., reference characters 28 and 32 in FIG. 1A) configured to receive and store materials from the fine filtration module(s) 26a-d. As shown in FIG. 1C, the collectors 28/32 may be ring-shaped, circular (pan-shaped), or cylindrical, and are generally continuous around the central axis 14.

For example, as shown in FIG. 1C, the system may have a first ring-shaped collector 32 configured to collect effluent material (e.g., permeate containing solids smaller than 0.1 µm, substantially clean or filtered water, etc.), which is separated from the mixture in fine filter(s) 26a-d. The permeate or substantially clean water may flow from the fine filter(s) 26a-d into ring shaped collector 32 through a conduit (e.g., spout, pipe, tube, or other device) 35 (FIG. 1A) configured to allow the separated liquid to flow freely into the collector 32. The ring-shaped collector may have any suitable size and shape that fits within the apparatus. However, in exemplary embodiments, and as shown in FIG. 1C, the ring-shape collector 32 forms a fixed ring around the central axis 14. Although not shown in the figures, in one variation, the collector is pan-shaped (circular) and has a central hole or opening at the bottom to facilitate transfer of the permeate from the collector to a storage tank or container (e.g., reference character 50 of FIG. 1C). In such variations, the pan-shaped collector may be sloped towards the central hole or opening. In addition, the pan-shaped collector is generally configured to have a diameter that spans a distance from spout, pipe, or tube 35, across axis 14, to a spout, pipe, or tube 35 associated with an opposing filter 26 180° on the other side of axis 14.

The ring-shaped collector 32 may have a diameter of 5 to 15 feet (1.5 to 4.5 m), and the water-collecting portion of ring-shaped collector 32 may have a width of about 0.5 to 3 feet (15 to 90 cm), or any value or range of values therein, and a height of about 0.25 to 3 feet (7 cm to 1 m), or any value or range of values therein. The ring-shaped collector 32 may be made of metal, plastic, ceramic (clay), rubber or any other suitable material known in the art. In some exemplary embodiments, the ring-shaped collector 32 may have a protective and/or non-stick coating on its interior and/or exterior surfaces. The spout, pipe, or tube 35 may comprise, metal, plastic, ceramic, rubber, or any other suitable material, and may include a protective and/or non-stick coating on its interior and/or exterior surfaces. In addition, the spout, pipe, or tube 35 may have a diameter of from about 1 to about 6 inches (2.5 to 15 cm), or any value therein.

Referring again to FIG. 1C, in some embodiments, the apparatus may include a plurality (or network) of outlets, pipes, tubes, or other drainage device(s) 45 configured to transport the permeate or substantially clean water from the ring-shaped collector 32 to one or more filtered water tanks 50 for storage, disposal, or additional processing. In exemplary embodiments, the ring-shaped collector 32 has a plurality of openings to the pipes or tubes 45. The openings in ring-shaped collector 32 are shown as circles in collector 32 in FIG. 1C. In some variations, the ring-shaped collector 32 can be slanted towards the openings and/or have raised parts in between the openings. Although FIG. 1C shows an embodiment having 4 openings, outlets and/or pipes connected to the ring-shaped collector 32, the invention is not limited as such. On the contrary, the ring-shaped collector 32 may have as many outlets, pipes, tubes, or drainage devices as desired, and the outlets, pipes, tubes, and/or drainage devices may be arranged at any desired location along the ring-shaped collector 32. The collector 32 may have the same shape and/or dimensions as collector 28, or collector 32 may have a different shape and/or dimensions, as desired.

The water storage tank(s) 50 may have any size or shape suitable for storing the permeate or substantially clean water produced by the filtration system. For example, the water storage tank(s) may have square, rectangular, circular, oval, or other shape, and may have a length, width, height, and/or diameter of from about 5 to 100 feet (150 cm to 30 m), or any value or range of values therein. The tank may comprise any suitable material for storing a liquid (e.g., plastic, metal, rubber, ceramic [clay], or combinations thereof), and may further include a pump or other mechanism for removing or transporting the permeate or clean water to another location for use and/or further processing. In some embodiments (for example, those including a pan-shaped collector), a central outlet or opening in the collector (or in the network of pipes or tubes connected thereto) may serve as an inlet to the water storage tank (which may be underground).

Referring again to FIG. 1A, the system may also include a second ring-shaped collector 28 that is configured to collect and/or store the concentrated effluent material (the concentrate) separated from the filtered mixture in the fine filtration module 26. The concentrate can flow from the fine filtration module 26 through a spout, pipe, or tubing 34. The spout, pipe, or tubing may comprise any suitable material described herein and may have a protective and/or non-stick coating on its interior and/or exterior surfaces. In some exemplary embodiments, the apparatus may also include a valve 27 configured to control the flow of concentrate from the fine filtration module 26 into the spout, pipe, or tubing 34. The spout, pipe, or tubing 34 may have a diameter of from about 1 to about 6 inches (2.5 to 15 cm), or any value therein.

In exemplary embodiments, and as shown in FIG. 1C, the second collector 28 generally forms a fixed ring around the central axis 14 and the first ring-shaped collector 32, and is configured to collect waste materials filtered from the filtration modules 26*a-d*. The second ring-shaped collector 28 may have a diameter of 6 to 18 feet (1.5 to 6 m), and the water-collecting portion of the second ring-shaped collector 28 may have a width of about 0.5 to 3 feet (15 to 100 cm), or any value or range of values therein, and a height of about 0.25 to 1 foot (7 to 30 cm), or any value or range of values therein. Although not shown in the figures, and also as discussed above with regard to the first collector 32, in some implementations, the second collector is pan-shaped (circular) and has a central hole or opening at the bottom to facilitate transfer of waste material from the collector to one or more waste containers. The pan-shaped collector may be sloped towards the central hole or opening, and is generally configured to have a diameter that spans a distance from spout, pipe, or tube 34, across axis 14, to a spout, pipe, or tube 34 associated with an opposing filter 26. The second collector 28 may be made of metal, plastic, ceramic (clay), or any other suitable material known in the art. In some exemplary embodiments, the second ring-shaped collector 28 may have a protective and/or non-stick coating on its interior and/or exterior surfaces.

Referring now to FIG. 1C, in some variations, the apparatus may also include a second plurality (or network) of outlets, pipes, or tubes 40*a-b* configured to transport the concentrate from the ring-shaped collector 28 to one or more waste containers for disposal or further processing. As discussed above with regard to the ring-shaped collector 32, the second ring-shaped collector 28 may also have as many outlets, pipes, tubes, or drainage devices as desired, and the outlets, pipes, tubes, and/or drainage devices may be arranged at any desired location along the ring-shaped collector 32. The directionality of the flow of concentrate may be controlled by arranging the second network of outlets, pipes or tubes 40*a-b* at an angle relative to one or more collection points so that the concentrate flows from the inlet toward the collection point(s). In one alternative embodiment, the system may also include a pumping mechanism at one or more locations along the network of pipes 40*a-b* to help move the concentrate and control the direction and rate of the flow.

The size of the present water treatment apparatus or system is flexible, and can be constructed from a small size to a large size, depending on the space available for the system and the amount of waste water that will be processed by the apparatus. For example, in exemplary embodiments, the water treatment apparatus may be built or installed in the basement (or other room) of a building or structure, and may be about the size of a typical bedroom (e.g., 10 feet by 10 feet [3 m by 3 m], 12 feet by 18 feet [3.5 m by 5.5 m], 14 feet by 14 feet [4 m by 4 m], etc.). In addition, multiple systems may be used in some situations.

Larger systems may be useful in buildings or situations where a large volume of waste water will be produced or processed. For example, a larger system may be installed for use in a large apartment or other high-rise building (e.g., comprising 2 or more buildings and/or units, etc.), institutions (e.g., schools, universities, hospitals, prisons, etc.) and large farms or agri-businesses. Smaller systems may be useful in buildings or situations where a smaller volume of waste water will be produced or processed, such as small apartment complexes or other low-rise buildings (e.g., comprising 2-4 apartments or 2-8 office units, etc.), small businesses, multiple family dwellings, etc. Smaller systems may also be useful for processing rain water runoff, or for use in relatively small (e.g., less than or equal to 1 to 5 acres) gardening applications.

Figure 2A:
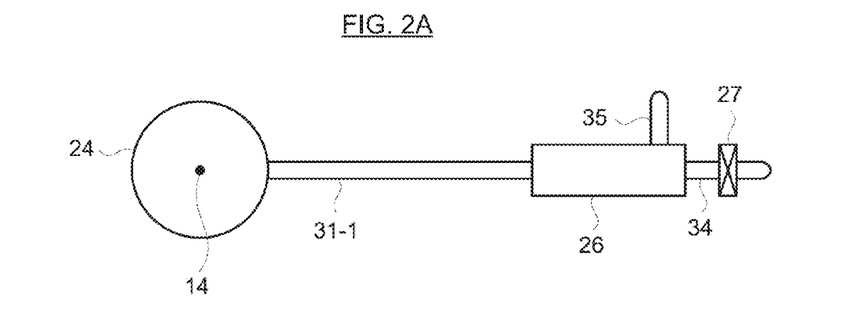
FIGS. 2A-2C show alternative embodiments for the arrangement of the fine filter and lower chamber for the lower portion of the present waste water treatment system.
Figure 2B:
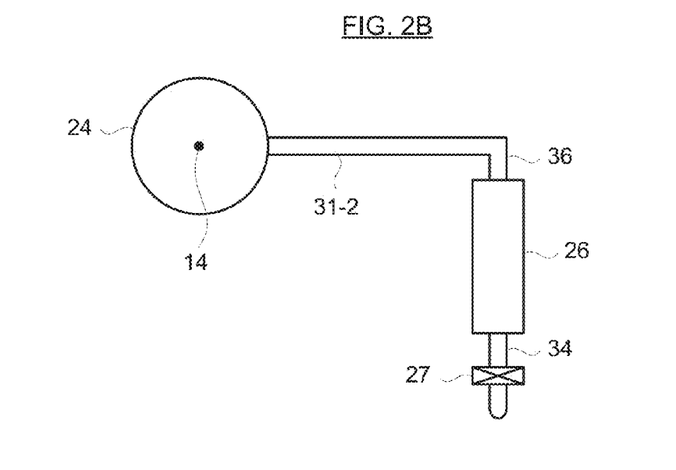
Figure 2C:
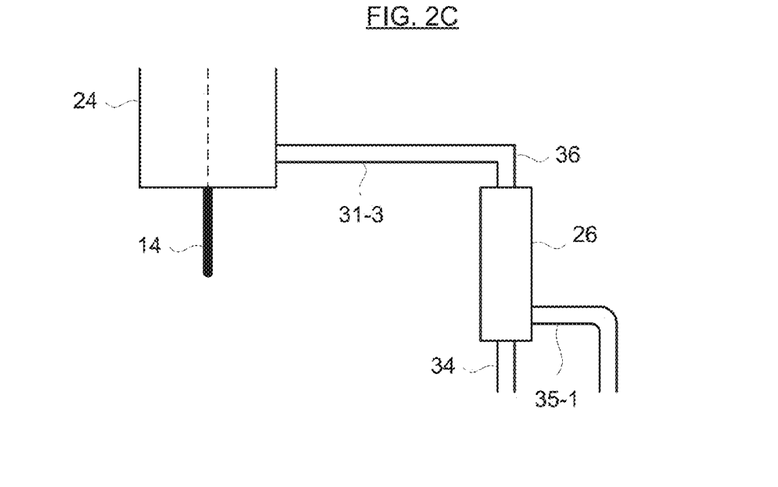

Alternative embodiments for the arrangement of the fine filter 26 and lower chamber 24 are shown in FIGS. 2A-2C. For example, in FIG. 2A, to increase the centrifugal force applied to filter 26 (as well as to the water passing through filter 26), the conduit (e.g., tube or pipe) 31-1 has a greater length than that of conduit 31 in FIGS. 1A and 1C. For example, the conduit 31 may have a length of from about 1 to about 6 feet (30 to 200 cm), or any value therein. In addition, "clean" water collection conduit 35 may be positioned on the exterior of the filter 26 at a more lateral or horizontal angle, in which case the direction of rotation of the apparatus around central axis 14 is opposite to the direction that conduit 35 extends from the filter 26.

FIG. 2B shows a top view of an alternative embodiment in which the conduit 31-2 has a greater length than that of conduit 31 in FIGS. 1A and 1C, and has a bent or angled portion 36, generally in which the filter 26 points away from the direction of rotation around axis 14. While the exemplary bent/angled portion 36 is shown as having a right angle, any angle of greater than 0° and up to 90° (or any angle within that range) can also be effective. In one embodiment, the portion of conduit 31 from the lower chamber 24 to the bent/angled portion 36 may have a length of from about 1 to about 5 feet (30 to 150 cm). Conduit 35 is positioned under the filter 26, as in FIGS. 1A and 1C. Such an embodiment may increase the centrifugal force applied to filter 26, as well as to the water passing through filter 26, while at the same time reducing the amount of floor space used or consumed by the apparatus.

FIG. 2C shows a side view of a further alternative embodiment in which the conduit 31-3 also has a greater length than that of conduit 31 in FIGS. 1A and 1C, but has a bent or angled portion 36 that directs the filter 26 towards the floor of the room in which the apparatus is located. In one embodiment, the portion of conduit 31 from the lower chamber 24 to the bent/angled portion 36 may have a length of from about 1 to about 4 feet (30 to 120 cm). Conduit 35-1 is on the exterior of the filter 26, so the relative locations of the clean water collection ring 32 and the concentrate collection ring 28 is reversed relative to FIGS. 1A and 1C (e.g., the concentrate collection ring 28 is on the inside). While the exemplary bent/angled portion 36 is shown as having a right angle, any angle of at least about 45° and up to 90° (or any angle within that range) can also be effective. Angles of less than 45° advantageously include a conduit on the exterior of the filter 26 oriented toward the inside of the apparatus, so that the relative locations of the clean water collection ring 32 and the concentrate collection ring 28 are the same as FIGS. 1A and 1C. Such an embodiment may increase the centrifugal force applied to filter 26, and allow gravity to assist with removal and/or collection of the concentrate and clean water from the filter 26, while at the same time reducing the amount of floor space used or consumed by the apparatus.

An Exemplary Method of Processing Waste Water

A second aspect of the present invention relates to a method of processing or treating waste water. In general, the method comprises (1) introducing waste water into one or more chambers operably connected to a plurality of filters arranged radially around a central axis, (2) rotating the plurality of filters at a sufficient rotational speed to pass a filtered mixture through at least one of the filters, where the filtered mixture has particles therein with a size less than a first minimum size, and each filter is configured to retain elements of the waste water having a size greater than the first minimum size, (3) transferring the filtered mixture to a plurality of filtration modules arranged radially around the central axis, and (4) rotating the filtered mixture at a sufficient rotational speed to separate a concentrate from the filtered mixture and produce substantially clean water from the filtered mixture, where the concentrate has particles therein with a size greater than a second minimum size, and the second minimum size is significantly smaller than the first minimum size.

Figure 3:
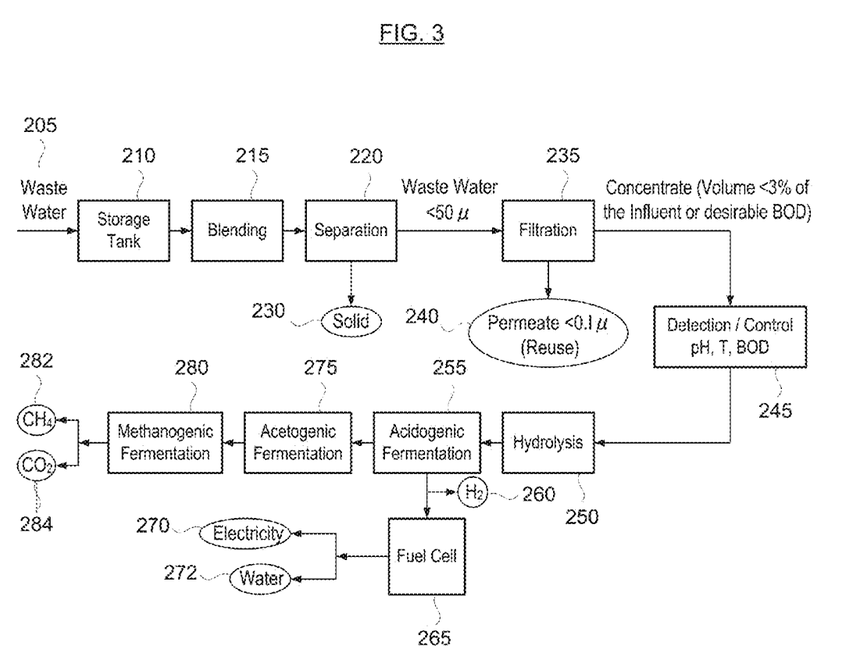
FIG. 3 is flowchart illustrating an exemplary method of waste water treatment, power generation, and methane production according to the present invention.

The exemplary method is described in detail herein with regard to the apparatus shown in FIGS. 1A-1C (as described in detail above with regard to an exemplary apparatus) and the flowchart of FIG. 3. Referring to FIG. 3, the method comprises introducing waste water 205 into a storage tank at 210 (e.g., mixing chamber 12 of FIG. 1A), for example, through an inlet (e.g., reference character 11 of FIG. 1A). As described in detail above with regard to the exemplary apparatus, the storage tank or mixing chamber 12 is generally continuous around a rotatable central axis 14 (e.g., cylindrical or toroidal; as shown in FIG. 1A). In some embodiments, large objects in the waste water (e.g., greater than 1 inch [2.5 cm] in length and/or width) may first be removed by passing the waste water through a wire or mesh screen.

Referring again to FIG. 3, the method may further comprise mixing or blending the waste water 215 (for example, in the mixing chamber 12 of FIG. 1B) using one or more rotating blades, paddles, beaters, or other suitable mixing mechanism (e.g., reference characters 13a-c of FIG. 1B). The blades or other mixing mechanism may be attached or otherwise associated with the rotatable central axis (see, e.g., central axis 14 FIGS. 1A-1B) that rotates or spins the blades, filters, and/or chambers of the apparatus at a rate suitable to mix, blend, and/or suspend solids and other filterable components in the waste water. For example, the method may include operating a device (e.g., a motor, hand crank, foot pedal, etc.) that provides the rotational force for the mixing mechanism (e.g., by turning the central axis or shaft 14, as previously described herein with regard to the exemplary apparatus).

Referring back to FIG. 3, the method further comprises separating the blended or mixed waste water at 220. For example, separating the waste water at 220 may comprise filtering the waste water through one or more filtering device (s) (e.g., filter or filter bag 20 of FIG. 1A). Thus, separating the waste water at 220 generally comprises retaining elements of the waste water having at least a first minimum size (e.g., materials greater than 10 µm, at least 50 µm, etc., in length and/or width) in the filtering device(s), and allowing the remaining material in the waste water mixture (including the fluids) to pass through.

In one exemplary embodiment, separating the waste water at 220 comprises passing the waste water through one or more coarse filtration bags or other filtration devices, and rotating the bags or other filtration devices about the central axis (reference character 14 of FIG. 1A). The filter bags or other filtration devices retain the solid materials (e.g., materials at least 10 µm, 50 µm, or any other length and/or width of about 100 µm or less, etc.) in the waste water, and allow the remaining fluid to pass through. The fluid that passes through may be collected in a chamber (e.g., chamber 19 in FIGS. 1A-B) for additional processing.

Referring to FIG. 3, separating the waste water at 220 may further comprise rotating the coarse filtering device(s) at a sufficient rotational speed (e.g., 50 to 10,000 rpm, 100 to 1,000 rpm, 150 to 500 rpm, etc.) to pass the waste water through the coarse filtering devices. For example, referring to FIG. 1B, rotating the coarse filtering device(s) 20a-d comprises rotating the central shaft or axis 14 to which the coarse filtering device(s) 20a-d are directly or indirectly connected.

In some instances, the solid matter (e.g., particulates having a size greater than a first minimum size, such as about 50 µm) separated from the waste water at 220 can be removed from the system as a by-product of the process. Thus, the method may further comprise removing such solid matter (e.g., by removing the filters or bags from the apparatus) and optionally reusing or recycling the solid matter, for example, as fertilizer or gardening. For example, the bag(s) or other filtration device(s) can be detached from the apparatus and removed from the chamber when they are full. In an embodiment that periodically removes and replaces the filtration devices(s), the solid content of the waste water can be estimated or measured over time. The volume of the filtration devices (bags) and the flow rate of the waste water can also be measured and/or estimated. The time required to fill the filtration devices to a predetermined level (e.g., 90%, 95%, 98%, etc.) can be calculated using the estimated and/or calculated values of the solid content of the waste water, the filtration device volume, and the waste water flow rate, and the water filtration apparatus can be stopped when the predetermined fill level has been reached. The opening of the filtration device may be automatically secured by a device such as an elastic band that automatically closes the opening of the filtration device when disengaged from the connector, to prevent spillage of the filtration device's contents. The bag(s) or other filtration device(s) can then be replaced with empty (e.g., new or recycled) bag(s) or filter(s). If desired, the solid matter (e.g., including the bags and/or filters) can be transported to a remote location for further processing by a disposal company.

Referring again to FIG. 3, after separating the waste water at 220, the method further comprises filtering the waste water free of particulates or contaminants having a size greater than the first minimum size at 235. For example, filtering the waste water separated from particulates or contaminants having a size greater than the first minimum size may comprise passing the waste water through fine filtration modules, cartridges, membranes, or other similar filters known in the art (e.g., 26a-d of FIG. 1B). The method may further comprise passing, flowing, or otherwise transporting the waste water from a collection chamber to the fine filtration module(s). Specifically, filtering the waste water separated from relatively large particulates may include rotating a plurality of the filtration modules about the central axis or shaft (e.g., axis 14), passing water or fluid in the waste water through a membrane or other filter material in the filtration modules, and concentrating particulates and/or contaminants having a size less than the first minimum size but greater than a second, maximum size (e.g., for particulates and/or contaminants in the water that passes through the membrane or other filter material).

In general, as shown in FIG. 3, the filtering process 235 divides the waste water into a permeate 240 and a concentrate. For example, the permeate 240 may comprise or consist essentially of water that contains particulates with a size less than a second, maximum size, such as 0.1 μm, but not larger particles or contaminants, and the concentrate generally comprises water containing particles greater than or equal to the second, maximum size (e.g., 0.1 μm). Typically, the volume of the concentrate is less than 3% of that of the influent (or desirable Biological Oxygen Demand [BOD]). The permeate 240 (e.g., clean water) can then be collected and reused or further processed. For example, the method may comprise collecting the permeate in a storage tank or other suitable container, and subsequently pumping or otherwise transporting the permeate elsewhere for use. Thus, in such embodiments, the method may further comprise recycling and/or purifying the permeate or filtered water, and using the permeate or filtered water for landscaping and/or domestic use, or if acceptable (e.g., after further purification and/or decontamination [e.g., pasteurization]), for drinking and cooking, as previously described herein.

In some embodiments, the method further comprises transporting or otherwise removing the concentrate from the fine filtration modules (26a-d of FIG. 1C), and collecting or storing the concentrate (e.g., in a second tank or other suitable collection structure e.g., reference character 28 of FIG. 1C) for disposal or additional processing as described herein.

In embodiments comprising additional processing, the collected concentrate can undergo a detection and/or control process at 245 of FIG. 3. Such process(s) may determine the flow rate(s), pH level(s), temperature, and/or BOD (which is a measure of the level of pollution) of the concentrate. Then, at 250, the method may comprise hydrolyzing the concentrate. For example, hydrolyzing the concentrate may comprise treating or otherwise exposing the concentrate to a hydrolyzing agent such as (1) bacteria known to hydrolyze contaminants and/or waste present in the concentrate, or (2) one or more hydrolyzing enzymes. In one embodiment, the concentrate may serve as a medium for culturing bacteria that hydrolyze the contaminants and/or waste, alone or in combination with one or more sugars (e.g., glucose), salts (e.g., NaCl) and/or buffers (e.g., sodium pyruvate or sodium citrate). Similarly, enzymatic hydrolysis may benefit from the addition of one or more salts (e.g., NaCl) and/or buffers (e.g., $NaH_2PO_4$ and/or $Na_2HPO_4$). In some instances, the concentrate may be hydrolyzed using an aqueous acid or alkali, such as aq. HCl, aq. $H_2SO_4$, aq. $HNO_3$, aq. $H_3PO_4$, combinations of such acids, aq. NaOH, aq. KOH, aq. $NH_4OH$, etc., but these methods may be less preferred due to the toxic and/or caustic nature of such acids and bases, and the need in most cases for neutralization prior to further processing. Other certain chemicals and/or additives known or determined to have beneficial effects may also be introduced to the hydrolysis process (as well as to the mixing process 215 and/or the permeate 240, which may be stored for a period of time prior to reuse). In general, the hydrolysis process may be accomplished using any suitable process or method known in the art.

In further embodiments, the method may comprise fermenting the hydrolyzed concentrate. Fermenting may be accomplished using any suitable process or method known in the art. For example, in some exemplary embodiments, the method may comprise one or more acidogenic, acetogenic, and/or methanogenic fermentation processes at 255, 275, and 280, respectively, performed on the hydrolyzed concentrate. The hydrolyzed concentrate may serve as a medium for culturing bacteria or other microorganisms that are used in the fermentation processes, alone or in combination with one or more sugars (e.g., glucose), salts (e.g., NaCl) and/or buffers (e.g., sodium pyruvate or sodium citrate), or other certain chemicals and/or additives known or determined to have beneficial effects in such fermentation. For example, in one embodiment, the method comprises fermenting the hydrolyzed concentrate (from 250) by acidogenic fermentation 255, e.g., using acidogenic bacteria. In such embodiments, the hydrogen 260 produced by the acidogenic fermentation process can be collected, and electricity 270 and water 272 can then be generated from the collected hydrogen 260 (for example, using a fuel cell 265). In some instances, energy (e.g., heat, mechanical energy, etc.) can be generated instead of electricity, using known technology for converting hydrogen to heat, or electricity to mechanical energy.

In further embodiments, the method may comprise acetogenic fermentation 275 and/or methanogenic fermentation 280 of the hydrolyzed concentrate, directly or following acidogenic fermentation 255. Although any individual or combination of fermentation processes may be conducted, and in any order, the sequence 255-270-280 in FIG. 3 is believed to be the most efficient fermentation sequence. In a further embodiment, methane ($CH_4$) 282 and/or carbon dioxide ($CO_2$) 284 resulting from the methanogenic fermentation process 280 can be collected and used as a source of fuel and/or carbonation (e.g., as dry ice). For example, heat can be generated from the collected methane, either separately from or together with the $CO_2$. In a further embodiment, the $CO_2$ can be removed from the mixture of $CH_4$ and $CO_2$ by passing the mixture through a liquid $N_2$ trap. In the alternative, the carbon dioxide can be removed, for example, by bubbling the gas mixture through water or dilute alkali such as dilute aqueous ammonia/ammonium hydroxide, or by scrubbing the gas mixture by passing it over a carbon dioxide remover such as calcium hydroxide. In some instances, more sophisticated (e.g., catalytic and/or recyclable) $CO_2$ scrubbers may also be used.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

CONCLUSION/SUMMARY

Thus, the present invention provides apparatuses and/or systems for processing waste water and methods of water treatment. The apparatuses and/or systems of the present invention can be incorporated into localized green resource stations that can serve a single residential structure, a high-rise building, an industrial or research facility, or small communities. Such green resource stations can be self-contained, and there is no need to channel waste water or sewage to a remote location. Consequently, maintenance of the station is relatively simple, and the costs associated with building and maintaining a conventional water treatment station are significantly reduced.

The apparatuses and methods of the present invention advantageously produce reusable clean water and renewable energy, reduce pollution and greenhouse gases, reduce waste odors and pathogens, and transform waste into valuable biofertilizer. In addition, the methods and systems of the present invention can reduce the retention time of waste water, and may increase the production rate or yield of the useful end-products of the process, for example, power generated from a fuel cell, clean water, and biogases, including methane and carbon dioxide, and usable fertilizer.

What is claimed is:

1. An apparatus, comprising:
   a) a first chamber for receiving waste water;
   b) a plurality of filters, arranged radially around a central axis, configured to receive the waste water from the first chamber and, upon being rotated around the central axis, retain elements of the waste water having at least a first minimum size and to allow a filtered mixture to pass through, the filtered mixture having particles therein with a size less than the first minimum size;
   c) a second chamber configured to collect the filtered mixture;
   d) a connector path configured to carry the filtered mixture from the second chamber; and
   e) a plurality of filtration modules, arranged radially around the central axis, configured to receive the filtered mixture at a near end of each filtration module to the central axis and, upon being rotated around the central axis, separate a concentrate from the filtered mixture and produce substantially clean water from the filtered mixture, the concentrate having particles therein with a size greater than a second minimum size, the second minimum size being significantly smaller than the first minimum size, and each filtration module having:
      i) at least one porous filter separating an inner chamber of the filtration module from an outer chamber of the filtration module and allowing a permeate to pass from the inner chamber into the outer chamber,
      ii) a permeate outlet connected to the outer chamber that transports the permeate away from the outer chamber, and
      iii) a concentrate outlet at a distal end of the inner chamber and/or the porous filter.

2. The apparatus of claim 1, further comprising (1) a rotating mechanism configured to rotate the filters and the filtration modules around the central axis, and (2) a clutch configured to control a rotational speed of the filters around the central axis relative to a rotational speed of the filtration modules around the central axis.

3. The apparatus of claim 1, further comprising (1) a blade or paddle configured to mix the waste water in the first chamber, and (2) a rotating mechanism configured to move the blade or paddle.

4. The apparatus of claim 1, wherein the first minimum size is at least about 10 µm and the second minimum size is at most about 1 µm.

5. The apparatus of claim 1, further comprising a valve at a distal end of the filtration module configured to control a rate at which the concentrate flows from the filtration module.

6. The apparatus of claim 5, further comprising a collection area downstream from the valve, the collection area configured to collect the concentrate.

7. The apparatus of claim 1, further comprising a third chamber configured to hydrolyze the concentrate.

8. The apparatus of claim 7, further comprising a fourth chamber configured to perform acidogenic fermentation on the hydrolyzed concentrate.

9. The apparatus of claim 8, further comprising a fifth chamber configured to perform acetogenic fermentation on the hydrolyzed, acidogenically fermented concentrate.

10. The apparatus of claim 9, further comprising a sixth chamber configured to perform methanogenic fermentation on the hydrolyzed, acidogenically and acetogenically fermented concentrate.

11. The apparatus of claim 10, further comprising a carbon dioxide remover or scrubber configured to remove $CO_2$ from a mixture of $CH_4$ and $CO_2$ resulting from the methanogenic fermentation.

12. The apparatus of claim 8, further comprising a fuel cell configured to generate electricity and water from hydrogen produced by the acidogenic fermentation.

13. The apparatus of claim 1, further comprising a plurality of collectors configured to receive and store or transfer materials from the plurality of filtration modules.

14. The apparatus of claim 13, wherein a first one of the plurality of collectors is configured to receive and store or transfer permeate separated from the filtered mixture by the plurality of filtration modules, and a second of the plurality of collectors is configured to receive and store or transfer concentrated effluent material from the plurality of filtration modules.

15. The apparatus of claim 14, further comprising one or more water storage tanks downstream from the first one of the plurality of collectors.

16. The apparatus of claim 15, wherein the water storage tank(s) have a length, width, height, and/or diameter of from 150 cm to 30 m.

17. The apparatus of claim 1, wherein the plurality of filters comprises at least four filters, and the plurality of filtration modules comprises at least four filtration modules.

18. The apparatus of claim 1, wherein each of the plurality of filters are identical or substantially identical to each other, and each of the plurality of filtration modules are identical or substantially identical to each other.

19. The apparatus of claim 1, wherein the central axis is from about 90 cm to 3 m in length and about 2.5 to 15 cm in diameter.

20. The apparatus of claim 1, wherein each of the first and second chambers is continuous around the central axis, the first chamber has a radius of 30 to 60 cm and a height of 30 to 90 cm, and the second chamber has a radius of 30 cm to 1 m and a height of 30 cm to 1.5 m.

21. the apparatus of claim 1, wherein each of the filtration modules has a cylindrical shape with a length of 30 cm to 1.5 m, and a width or diameter of 10 to 50 cm.

* * * * *